(12) United States Patent
Torizuka et al.

(10) Patent No.: US 6,440,429 B1
(45) Date of Patent: Aug. 27, 2002

(54) EMULSIFIED, WATER-IN-OIL TYPE COMPOSITION AND SKIN COSMETIC PREPARATION

(75) Inventors: Makoto Torizuka; Hirohisa Suzuki; Kana Fujiwara, all of Tokyo; Takashi Oda, Wakayama; Nobushige Tanaka, Wakayama; Katsuhiko Rindo, Wakayama, all of (JP)

(73) Assignee: Kao Corporation, Tokyo (JP)

( * ) Notice: Subject to any disclaimer, the term of this patent is extended or adjusted under 35 U.S.C. 154(b) by 633 days.

(21) Appl. No.: 08/709,218

(22) Filed: Sep. 6, 1996

(30) Foreign Application Priority Data

Sep. 6, 1995 (JP) .............................. 7-228908

(51) Int. Cl.$^7$ ................................. A61K 7/00
(52) U.S. Cl. ................ 424/401; 424/59; 424/70.11; 424/70.12; 424/70.121; 424/70.122
(58) Field of Search .............. 424/401, 69, 70.1, 424/70.11, 70.12, 70.121, 70.122; 514/937

(56) References Cited

U.S. PATENT DOCUMENTS 5,104,646 A * 4/1992 Bolich, Jr. et al. ............ 424/70

FOREIGN PATENT DOCUMENTS

| EP | 0 260 641 | 3/1988 |
|---|---|---|
| EP | 0 291 683 | 11/1988 |
| EP | 0 412 704 | 2/1991 |
| EP | 0 640 643 | 3/1995 |
| WO | WO 95/06078 | 3/1995 |
| WO | WO 95/06079 | 3/1995 |

OTHER PUBLICATIONS

Patent Abstracts of Japan; Yoshimatsu Akira; "Cosmetic"; JP 05 112423; May 7, 1993.
Patent Abstracts of Japan; Oda Taku; "Preparation of New Organopolysiloxane", JP 04 085335; Mar. 18, 1992.
Patent Abstracts of Japan; Oda Taku; "New Organopolysiloxane and Preparation Thereof", JP 04 085334; Mar. 18, 1992.
Patent Abstracts of Japan; Kondo Akihiro; "New Organopolysiloxane and Production Thereof", JP 02 276824; Nov. 13, 1990.
JP 61–218509 (Sep. 29, 1986) Abstract.
JP 64–63031 (Mar. 9, 1989) Abstract.
JP 1–180237 (Jul. 18, 1989) Abstract.

* cited by examiner

Primary Examiner—Jyothsna Venkat
(74) Attorney, Agent, or Firm—Oblon, Spivak, McClelland, Maier & Neustadt, P.C.

(57) ABSTRACT

An emulsified, water-in-oil type composition comprises the following components (A), (B), (C) and (D):

(A) an oil phase,
(B) a high molecular compound having orientation to oil-water interfaces,
(C) a lower alcohol, and
(D) water.

A skin cosmetic preparation containing the emulsified, water-in-oil type composition is also disclosed.

24 Claims, No Drawings

EMULSIFIED, WATER-IN-OIL TYPE COMPOSITION AND SKIN COSMETIC PREPARATION

BACKGROUND OF THE INVENTION a) Field of the Invention

This invention relates to an emulsified, water-in-oil type composition, which can give refreshed feeling of use without stickiness and is excellent in emulsion stability, and also to a skin cosmetic preparation containing same.

b) Description of the Related Art

As oil components usable in emulsified, water-in-oil compositions, many hydrocarbon oils such as liquid paraffin and squalane are known to date. When they are applied to skin cosmetic preparations, they cover the skin surface with an oil film and prevent evaporation of moisture so that they are effective for skin roughness and the like. Facial cosmetic preparations making use of these oil components have high treatment effects, while makeup cosmetic preparations with such oil components employed therein have excellent water repellency and feature long-lasting makeups.

On the other hand, emulsified, water-in-oil type cosmetic preparations added with silicone oils as oil components can give smooth feeling of use and are excellent in water repellency. In particular, cosmetic preparations added with volatile silicones feature good spreadability upon application and, as they are spread, the volatile silicone oils are allowed to evaporate, resulting in a reduction in the oils remaining on the skin surfaces. These cosmetic preparations therefore feature good adhesion, high durability against sebum and sweat, and long-lasting makeups. Further, combined use of a lower alcohol such as ethanol makes it possible to give pleasant refreshness and refreshed feeling of use because of the heat of vaporization taken away for their high volatility.

However, the addition of a lower alcohol such as ethanol makes it very difficult to obtain a stable water-in-oil emulsion system. An emulsified, water-in-oil cosmetic preparation which contains such a lower alcohol at a high concentration and has excellent stability has not been obtained despite the existence of a strong desire therefor. Conventionally known methods for obtaining emulsified, water-in-oil type cosmetic preparations having good stability include inter alia a method in which the content of a wax is increased to achieve solidification, a method making use of silica, and methods in which stable emulsification is conducted using a clay mineral and a polyoxy-alkylene-modified silicone [Japanese Patent Application Laid-Open (Kokai) No. SHO 61-218509, Japanese Patent Application Laid-Open (Kokai) No. SHO 64-63031, and Japanese Patent Application Laid-Open (Kokai) No. HEI 1-180237]. When a lower alcohol such as ethanol is added to provide refreshed feeling, however, these methods are still unable to provide stable emulsion products and are hence accompanied by a problem in the storage stability of emulsion products. Furthermore, concurrent use of a silicon e oil and ethanol or the like leads to a significant reduction in emulsion stability, so that the problem of separation becomes more dominant. Therefore, those added with ethanol or the like are generally accompanied by the irksome problem that users must shake them before use.

SUMMARY OF THE INVENTION

An object of the present invention is therefore to provide an emulsified, water-in-oil composition, which can give refreshed feeling of use, does not become sticky with time, and is excellent in emulsion stability, and also a skin cosmetic preparation containing the emulsified, water-in-oil composition, and also a skin cosmetic preparation containing the emulsified, water-in-oil composition.

Under the above-described current circumstances, the present inventors have carried out an extensive investigation. As a result, it has been found that use of a high polymer compound having orientation to oil-water interfaces, for example, one or more high molecular compounds—which are selected from copolymers capable of forming intra- and intermolecular crosslinks through bonds other than covalent bonds, copolymers containing hydrophilic segments soluble or dispersible in water or a lower alcohol and copolymers containing hydrophilic segments and an organopolysiloxane segment—as an emulsifier or emulsification aid can provide a cosmetic preparation which is excellent in emulsion stability even if a lower alcohol such as ethanol is included and, when applied to a skin cosmetic preparation, which gives refreshed feeling of use and remains stick-free even if time goes on, leading to the completion of the present invention.

Namely, the present invention provides an emulsified, water-in-oil type composition comprising the following components (A), (B), (C) and (D):

(A) an oil phase, (B) a high molecular compound having orientation to oil-water interfaces, (C) a lower alcohol, and (D) water; and a skin cosmetic preparation containing same.

The emulsified, water-in-oil type composition and skin cosmetic preparation containing same, both pertaining to the present invention, exhibit excellent emulsion stability, gives excellent refreshed feeling and is stick-free.

DETAILED DESCRIPTION OF THE INVENTION AND PREFERRED EMBODIMENTS

No particular limitation is imposed on the oil phase as the component (A) insofar as it is an oil component commonly employed in cosmetic preparations. Illustrative of the component (A) are solid or semisolid oils such as vaseline, lanolin, ceresin, microcrystalline wax, carnauba wax, candelilla wax, cholesterol esters, high fatty acids, and higher alcohols; liquid oils such as jojoba oil, castor oil, isopropyl myristate, octyldodecyl myristate, trimethylolpropane triisostearate, diisostearyl malate, isostearyl alcohol, oleyl alcohol, oleic acid, isostearic acid, myristic acid, stearic acid, squalane, liquid paraffin, ester oils, triglycerides, diglycerides, and perfluoropolyethers; and silicone oils such as dimethylpolysiloxane, dimethylcyclopolysiloxane, methylphenylpolysiloxane, methylhydrogenpolysiloxane, higher-fatty-acid-modified organopolysiloxanes, higher-alcohol-modified organopolysiloxanes, and trimethyl siloxysilicate. These oil components can be used either singly or in combination.

The component (A) preferably contains one or more silicone oils. Preferred exemplary silicone oils include volatile dimethylpolysiloxane and dimethylcyclopolysiloxane having structures of the following formula (13), respectively.

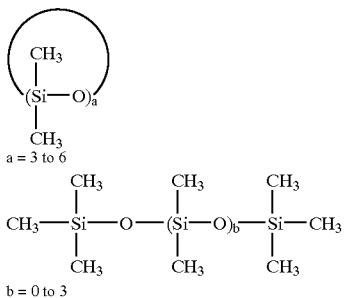

The proportion of the silicone oil is preferably 5 to 100 wt. % based on the oil as the component (A). The proportion of the whole oil including the silicone oil is preferably 10–90 wt. % based on the emulsified, water-in-oil type composition, with 10–85 wt. % being more preferably and 15–85 wt. % being particularly preferred.

No particular limitation is imposed on the high molecular compound as the component (B), which has orientation to oil-water interfaces. The high molecular compound is preferably a viscous liquid or solid copolymer which forms intra-molecular crosslinks and inter-molecular crosslinks through bonds other than covalent bonds, such as dipole-dipole interaction, hydrogen bonding and ion bonding. The high molecular compound is more preferably a copolymer, which is a solid at room temperature and under normal pressure and shows physical properties of undergoing neither rupture or plastic deformation in an elongation range of from 0 to 15% at 20° C. and 65% R.H., or a copolymer which contains hydrophilic segments and are soluble or dispersible in water or a lower alcohol. Notably, the high molecular compound can be a copolymer which contains hydrophilic segments and an organopolysiloxane segment.

Such a high molecular compound may desirably be soluble or completely dispersible in water or a lower alcohol, in other words, a high molecular compound whose crosslinks are readily cleaved in water or a lower alcohol. The term "lower alcohol" as used herein preferably means a $C_1$–$C_6$ alcohol.

Examples of the bonds other than covalent bonds include bonds which are readily cleaved in water or a lower alcohol, for example, ionic bonds, hydrogen bonds, hydrophobic interactions, dipole-dipole interactions, and bonds by van der Waals force, with ionic bonds, hydrogen bonds and dipole-dipole interactions being preferred. The organopolysiloxane useful in the present invention contains one or more kinds of functional groups which form such bonds.

Further, the high molecular compound (B) preferably has properties that it undergoes neither rupture nor plastic deformation in the elongation range of from 0 to 15% at 20° C. and 65% R.H. A polymer is generally known to restore its original shape when a deformation is small but to have difficulty in restoring its original when the deformation becomes greater. Such a deformation that does not permit restoration of the original shape is called a "plastic deformation". Hard and brittle polymers include those undergoing rupture before developing a plastic deformation. They are both unable to retain the original shape and are not suited as materials for protecting water droplets around them in a water-in-oil type emulsion. Accordingly, the above-described properties of the high molecular material having orientation to oil-water interfaces in the present invention is so-called rubber elasticity and are extremely important for being distributed around water droplets, forming protective films for the water droplets and hence preventing separation of the emulsified composition.

Whether or not a plastic deformation takes place within the elongation range of from 0 to 15% can be determined by a simple experiment, for example, as will be described next. Namely, a test piece of about 0.2 mm in thickness, 20 mm in length and 5 mm in width is provided. Under conditions of 20° C. and 65% R.H., the test piece is caused to elongate up to 3 mm (15%) at a crosshead speed of 20 mm/min while recording a stress-strain curve. After that, the cross-head is immediately caused to return to the original position at the same speed. Ten minutes later, the test piece is caused to elongate again. If the stress-strain curve at the time of the second elongation follows the same track as the first curve, the test piece can be considered to have completely restored from the deformation and to have not caused any plastic deformation. If a plastic deformation has taken place, on the other hand, the test piece has already undergone elongation in the first reciprocation so that in the second elongation, a stress is applied and as a result, the stress-strain curve does not follow the same track.

No particular limitation is imposed on the high molecular compound (B) insofar as it forms intramolecular crosslinks and inter-molecular crosslinks through bonds other than covalent bonds, such as dipole-dipole interaction, hydrogen bonding and ion bonding. To form intramolecular or inter-molecular crosslinks through bonds other than covalent bonds, it is necessary to contain certain polar functional groups in the copolymer at terminals or side chains thereof. When an organopolysiloxane segment is contained in the copolymer, another high molecular compound may be used as connecting groups between the organopolysiloxane segment and the polar functional groups.

Examples of such polar functional groups include those derived from N-acylalkyleneimines, pyrrolidone and the like as those producing dipole-dipole interactions. Illustrative of those forming hydrogen bonds are those containing amido groups, such as poly(meth)acrylamide mono- or di-($C_1$-$_4$alkyl)(meth)acrylamide such as polydimethylacrylamide and polydiethylacrylamide, poly-N-morpholine(meth) acrylamide, poly-N-vinylpyrrolidone, poly-N-vinylacetamide, poly(amino acid) and those containing hydroxyl groups, such as succharides and polyvinylalcohol. Further, illustrative of those forming ionic bonds are betaine polymers, e.g., carbobetaine, sulfobetaine and phosphobetaine; and amphoteric ionomers between anionic monomers such as (meth)acrylic acid and cationic monomers such as N,N-dimethylaminoethyl (meth)acrylate and N,N-dimethylaminopropyl (meth)acrylate; and amine oxides.

In the emulsified, water-in-oil composition according to the present invention, the high molecular compound, under the action of the hydrophilic segments contained in the high-molecular compound having orientation to oil-water interfaces, orientates to interfaces between water droplets and a continuous phase (outer phase=oil phase) in the w/o emulsion so that the high molecular compound can prevent coalescence, settling or the like of the water droplets. Further, at this time, the high molecular compound (B) acts as protective films of elastic nature for the water droplets. A w/o emulsion which contains ethanol and a silicone oil may separate due to coalescence or settling of water droplets by orientation of interfacial films which tends to occur by a conventional emulsifier. Since the high-molecular compound (B) serves as protective films of elastic nature against such separation, coalescence or settling of water droplets is prevented so that a stable emulsion product can be obtained. To obtain protective films of elastic nature for such water droplets, it is preferred for the polymer to contain hydrophilic segments which exhibit special properties.

As the high molecular compound (B), it is preferred to orientate to interfaces between the water droplets and the oil phase in the emulsified, water-in-oil composition so that protective films for the water droplet, said films being resistant to a lower alcohol (and also resistant to a silicone oil where the silicone oil is contained in the oil phase), are formed. It is preferred for the high molecular compound (B) to show rubber elasticity at room temperature and under normal pressure as a physical property of the high molecular compound (B) itself. This physical property of the high molecular compound (B) itself at room temperature and under normal pressure is however not essential, because even a high molecular compound unable to show rubber elasticity by itself may also be used provided that it distributes to the interfaces between the water droplets and the oil phase and brings about similar effects when it is caused to exist together with a substance forming the emulsified, water-in-oil composition, such as a lower alcohol and/or a silicone oil.

Specific examples of the hydrophilic segments include segments derived from one or more compounds or groups selected from terminal-blocked N-acylalkylene-imines, polyalkylene glycols, polyalkylene glycol monoalkyl ethers, acrylic acid, methacrylic acid, N,N-dimethylacrylamide, dimethylaminoethyl methacrylate, quaternary dimethylaminoethyl methacrylate, methacrylamide, N-t-butylacrylamide, maleic acid, maleic anhydride, half esters of maleic anhydride, crotonic acid, itaconic acid, acrylamide, acrylate alcohols, hydroxyethyl methacrylate, diallyldimethylammonium chloride, vinylpyrrolidone, vinyl ethers, vinylpyridine, vinylimidazole, styrenesulfonates, allyl alcohol, vinyl alcohol, vinyl caprolactam, N-alkylenecarbobetaines, or saccharide-derived residual groups.

Preferably, the hydrophilic segments can be those derived from one or more compounds or groups selected from N-acylalkyleneimines, polyalkylene glycols, polyalkylene glycol monoalkyl ethers, acrylic acid, N,N-dimethylacrylamide, dimethylaminoethyl methacrylate, quaternary dimethylaminoethyl methacrylate, vinylpyrrolidone, N-alkylenecarbobetaines, or saccharide-derived residual groups.

In the high molecular compound which is soluble or dispersible in water or a lower alcohol, contains hydrophilic segments and shows orientation to interfaces, the proportion of the hydrophilic segments may range from 1/50 to 20/1, preferably from 1/40 to 2/1 in terms of the polymerization ratio of the hydrophilic segments to the segments (including an organopolysiloxane segment) other than the hydrophilic segments and the molecular weight of the high-molecular compound may range from 500 to 500,000, preferably from 1,000 to 300,000, both from the viewpoint of obtaining a stable emulsion product.

Further, preferred examples of copolymers containing as a hydrophilic segment at least one segment derived from an N-acylalkyleneimine include those containing, in their molecules, at least one segment of a poly(N-acylalkyleneimine), which is formed of recurring units represented by the following formula (1):

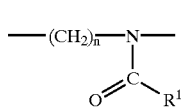

wherein $R^1$ represents a hydrogen atom, an alkyl group having 1 to 22 carbon atoms, a cycloalkyl group, an aralkyl group or an aryl group, and n stands for a value of 2 or 3, and an organopolysiloxane segment, in which the segment of the poly(N-acylalkyleneimine) containing the recurring units represented by the formula (1) is bonded via a hetero-atom-containing alkylene group to at least one terminal or side-chain silicon atom of the organopolysiloxane segment. From the standpoint of obtaining stable emulsion products, such poly(N-acylalkyleneimine)-modified silicones preferably can contain the poly(N-acylalkyleneimine) segments and the organopolysiloxane segment at a weight ratio of from 1/50 to 20/1, preferably from 1/40 to 2/1 and can have a molecular weight of from 500 to 500,000, preferably from 1,000 to 300,000.

Further, illustrative of the cycloalkyl group represented by $R^1$ in the formula (I) are those containing 3 to 6 carbon atoms, illustrative of the aralkyl group are phenylalkyl and naphthylalkyl, and illustrative of the aryl group are phenyl, naphthyl and alkyl-substituted phenyl. Examples of the hetero-atom-containing alkylene group which is bonded to at least one terminal or side-chain silicon atom in the organopolysiloxane segment include $C_{2-20}$ alkylene groups containing 1 to 3 nitrogen, oxygen and/or sulfur atoms. Specific examples include groups represented by the following formulas (3):

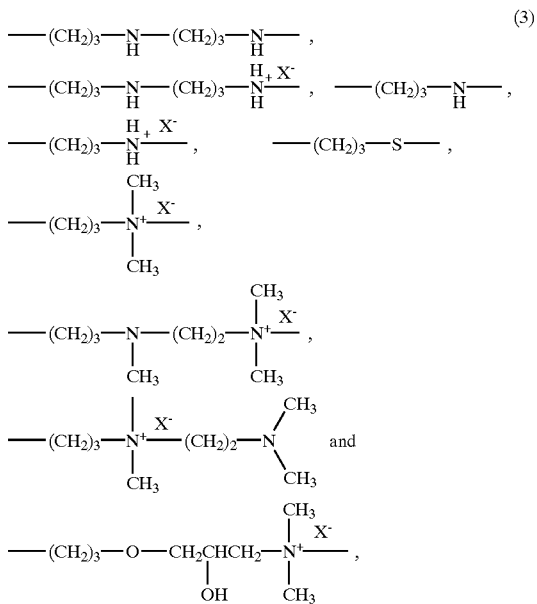

wherein $X^-$ represents a counter ion to a quaternary ammonium salt.

Preferred examples of such poly(N-acylalkyleneimine)-modified silicones include poly(N-formylethyleneimine)-modified silicone, poly(N-acetylethyleneimine)-modified silicone, poly(N-propionylethyleneimine)-modified silicone, poly(N-n-octanoylethyleneimine)-modified silicone, poly(N-n-dodecanoylethyleneimine)-modified silicone, poly(N-formylpropyleneimine)-modified silicone, poly(N-acetylpropyleneimine)-modified silicone, poly(N- propionylpropyleneimine)-modified silicone, poly(N-n-octanoylepropyleneimine)-modified silicone, and poly(N-n-dodecanoylpropyleneimine)-modified silicone.

The above-described poly(N-acylalkyleneimine)-modified silicones can be obtained by a known process [Japanese Patent Application Laid-Open (Kokai) No. HEI 2-276824, Japanese Patent Application Laid-Open (Kokai) No. HEI 4-85334, Japanese Patent Application Laid-Open (Kokai) No. HEI 4-85335, Japanese Patent Application Laid-Open (Kokai) No. HEI 5-112423, Japanese Patent Application Laid-Open (Kokai) No. HEI 7-133352, or the like]. For example, they can each be synthesized by the following process. First, the segment of the poly(N-acylalkyleneimine) formed of the recurring units represented by the formula (1) can be obtained by subjecting, to ring-opening polymerization, a cyclic imino ether compound represented by the following formula (14):

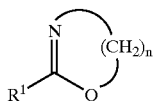

(14)

wherein $R^1$ represents a hydrogen atom or a $C_{1-22}$ alkyl, cycloalkyl, aralkyl or aryl group, and n stands for 2 or 3. The cyclic imino ether compound represented by the formula (14) can be a 2-oxazoline or 2-oxazine such as that to be exemplified below. Namely, illustrative of the cyclic imino ether compound are 2-oxazoline, 2-methyl-2-oxazoline, 2-ethyl-2-oxazoline, 2-propyl-2-oxazoline, 2-butyl-2-oxazoline, 2-pentyl-2-oxazoline, 2-heptyl-2-oxazoline, 2-octyl-2-oxazoline, 2-nonyl-2-oxazoline, 2-decyl-2-oxazoline, 2-undecyl-2-oxazoline, 2-dodecyl-2-oxazoline, 2-tridecyl-2-oxazoline, 2-tetradecyl-2-oxazoline, 2-pentadecyl-2-oxazoline, 2-hexadecyl-2-oxazoline, 2-heptadecyl-2-oxazoline, 2-octadecyl-2-oxazoline, 2-nonadecyl-2-oxazoline, 2-eicosyl-2-oxazoline, 2-heneicosyl-2-oxazoline, 2-docosyl-2-oxazoline, 2-benzyl-2-oxazoline, 2-phenyl-2-oxazoline, 2-naphthyl-2-oxazoline, 2-anthryl-2-oxazoline, 2-pyrenyl-2-oxazoline, 2-perylenyl-2-oxazoline, 2-cyclohexyl-2-oxazoline, 2-oxazine, 2-methyl-2-oxazine, 2-ethyl-2-oxazine, 2-propyl-2-oxazine, 2-butyl-2-oxazine, 2-pentyl-2-oxazine, 2-hexyl-2-oxazine, 2-heptyl-2-oxazine, 2-octyl-2-oxazine, 2-nonyl-2-oxazine, 2-decyl-2-oxazine, 2-undecyl-2-oxazine, 2-dodecyl-2-oxazine, 2-tridecyl-2-oxazine, 2-tetradecyl-2-oxazine, 2-pentadecyl-2-oxazine, 2-hexadecyl-2-oxazine, 2-heptadecyl-2-oxazine, 2-octadecyl-2-oxazine, 2-nonadecyl-2-oxazine, 2-eicosyl-2-oxazine, 2-heneicosyl-2-oxazine, 2-docosyl-2-oxazine, 2-benzyl-2-oxazine, 2-phenyl-2-oxazine, 2-naphthyl-2-oxazine, 2-anthryl-2-oxazine, 2-pyrenyl-2-oxazine, 2-perylenyl-2-oxazine, and 2-cyclohexyl-2-oxazine.

These cyclic imino ethers can be prepared, for example, by the process described in Liebigs Ann. Chem., pp. 996–1009 (1974).

These compounds can be used either singly or in combination as a monomer or monomers for ring-opening polymerization.

Examples of a polymerization initiator which can be used to subject the above-described cyclic imino ether to ring-opening polymerization include, but are not limited to, alkyl toluenesulfonates, dialkyl sulfates, alkyl trifluoromethanesulfonates, and alkyl halides. These initiators can be used either singly or in combination.

A molecular chain of a poly(N-acylalkyleneimine) can be obtained by subjecting the cyclic imino ether compound represented by the formula (14) to ring-opening polymerization while using such an initiator. This molecular chain can be either a homopolymer chain or a copolymer chain, and the copolymer chain can be either a random copolymer chain or a block copolymer chain.

The molecular weight of the molecular chain of the poly(N-acylalkyleneimine) is preferably 150 or higher but 50,000 or lower, more preferably 500 or higher but 10,000 or lower. A molecular weight lower than 150 no longer has properties of the poly(N-acylalkyleneimine), whereas a molecular weight higher than 50,000 leads to difficulty in preparation. Molecular weights outside the above range are therefore not preferred.

In the high molecular compound (B), the copolymer with one or more segments derived from the N-acylalkyleneimine as hydrophilic segment(s) can be obtained by reacting an active species for polymerization, said species being formed by subjecting the cyclic imino ether represented by the formula (14) to ring-opening polymerization, with an organopolysiloxane containing one or more functional groups reactive to the active species.

Illustrative of the functional groups reactive to the active species include primary, secondary or tertiary amino groups, a mercapto group, a hydroxyl group, and carboxylate groups. Of these, an amino group or a mercapto group is preferred. The organopolysiloxane which contains amino groups or mercapto groups in its molecule can preferably have a molecular weight of from 300 to 400,000, with a molecular weight in a range of from 800 to 250,000 being more preferred. The organopolysiloxane can be either linear or branched. As the molecular weight of the organopolysiloxane, a molecular weight lower than 300 is not preferred from the viewpoint of obtaining a stable emulsion product, but a molecular weight higher than 400,000 leads to a gel-like organopolysiloxane which is difficult to react. Accordingly, molecular weights outside the above range are not preferred.

The thus-contained amino or mercapto groups can be introduced into the backbone or the side chains.

The reaction between the organopolysiloxane containing amino or mercapto groups and reactive terminals of the poly(N-acylalkyleneimine) obtained by the cationic polymerization of the cyclic imino ether can be conducted as will be described below.

An initiator is dissolved in a polar solvent, preferably a single solvent such as acetonitrile, valeronitrile, dimethylformamide, dimethylacetamide, chloroform, methylene chloride, ethylene chloride, ethyl acetate or methyl acetate or, if necessary, a mixed solvent with another solvent, and the resultant solution is heated to 40 to 150° C., preferably 60 to 100° C. To the thus-heated solution, the cyclic imino ether represented by the formula (14) is poured at once or, if the reaction is violent, is added dropwise, followed by polymerization. The progress of the polymerization can be traced by quantitating the remaining amount of the cyclic imino ether, the monomer, by an analytical instrument such as gas chromatography. Even after the cyclic imino ether has been used up and the polymerization has been completed, the active species at each growing terminal still retains activity. Without isolation, the polymer solution is then mixed with an organopolysiloxane containing amino or mercapto groups in its molecule, followed by a reaction at 5 to 100° C., preferably 20 to 60° C. Although their mixing ratio can be suitably chosen as desired, it is preferred to react the poly(N-acylalkyleneimine) in a proportion of 0.1 to 1.3 mole equivalents per mole of the amino or mercapto groups in the organopolysiloxane. A proportion smaller than 0.1 mole equivalent leads to an unduly small modification degree, thereby making it difficult to impart the properties of the poly(N-acylalkyleneimine) as desired in the present invention. On the other hand, a proportion greater than 1.3 mole equivalents is unnecessary.

By a reaction such as that described above, a block copolymer or graft copolymer containing poly(N-acylalkyleneimine) segments as segments hydrophilic to the polydimethylsiloxane can be obtained.

In addition, it is also possible to use as the high molecular compound (B) a copolymer in which a group, which is represented by the following formula (4):

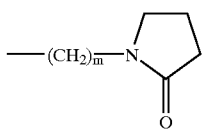

(4)

wherein m stands for an integer of from 1 to 8, is bonded to at least one terminal or side-chain silicon atom of an organopolysiloxane segment.

In the above copolymer, the number of silicon atoms to which the groups represented by the formula (4) are bonded preferably accounts for 10 to 90% (more preferably 40 to 80%) of the total number of silicon atoms in the molecule of said high molecular compound (B), and the copolymer preferably has a weight average molecular weight of from 1,000 to 500,000 (more preferably 5,000 to 300,000).

A weight average molecular weight of the organopolysiloxane containing the groups (4) smaller than 1,000 results in poor emulsion stability, whereas a weight average molecular weight greater than 500,000 leads to difficulty in preparation. If the number of silicon atoms to which the groups represented by the formula (4) are bonded is smaller than 10% of the total number of the silicon atoms in the molecule, no sufficient orientation to oil-water interfaces is brought about, resulting in poor emulsion stability. If the former number is greater than 90% of the latter number, the resulting organopolysiloxane shows unduly high water solubility, thereby making it difficult to exhibit emulsifiability.

The organopolysiloxane, which contains such groups (4), can be synthesized by a so-called hydrosilylating reaction in which, for example, an organohydrogenpolysiloxane such as that represented by the below-described formula (15) is used as a precursor and is reacted with an N-alkylenepyrrolidone such as that represented by the below-described formula (16). This hydrosilylating reaction can be conducted at room temperature to 100° C. in the presence of a transition metal complex like hydrogen hexachloro platinate as a catalyst while using, as a reaction solvent, a halogen-containing solvent such as dichloromethane, chloroform or 1,2-dichloroethane or an aliphatic ether such as tetrahydrofuran, diisopropyl ether or dibutyl ether.

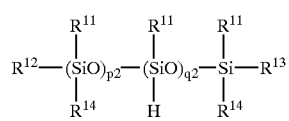

(15)

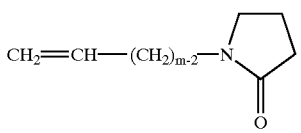

(16)

wherein $R^{11}$s may be the same or different and individually represents a saturated alkyl group or a phenyl group, $R^{12}$, $R^{13}$ and $R^{14}$ individually represents the same group as $R^{11}$s or a group selected from a $C_{1-22}$ saturated alkyl group or a phenyl group, p2 stands for an integer of from 30 to 3,000, q2 stands for an integer of from 60 to 1,500, and m has the same meaning as defined above.

Japanese Patent Application Laid-Open (Kokai) No. HEI 5-32784 discloses siloxane compounds analogous to the above-described organopolysiloxane and their preparation process. It is however silent about effects for suppressing separation of an emulsified, water-in-oil composition containing a lower alcohol (or, and also a silicone oil).

Furthermore, it is also possible to use as the high molecular compound (B) a copolymer in which a saccharide-derived residual group is bonded to at least one terminal or side-chain silicon atom of an organopolysiloxane segment.

With respect to this organopolysiloxane, a saccharide lactone amidoalkyl group (a group formed as a result of bonding between a saccharide lactone compound and an aminoalkyl group through an amide bond) can be mentioned as the saccharide-derived residual group. Further, preferred as the organopolysiloxane is one containing a silicone chain in a proportion of from 40 to 97 wt. % (more preferably 50 to 95 wt. %) and having a weight average molecular weight of from 1,000 to 500,000 (more preferably 5,000 to 300,000). A silicone chain in a proportion smaller than 40 wt. % leads to poor emulsion stability, while a silicone chain in a proportion greater than 97 wt. % results in a reduction in the orientation to water droplets, leading also to poor emulsion stability. Further, a weight average molecular weight lower than 1,000 results in poor emulsion stability while a weight average molecular weight higher than 500,000 leads to difficulty in preparation.

The organopolysiloxane, which contains such saccharide-derived residual groups bonded therein, can be prepared, for example, by reacting a saccharide lactone compound (which has been formed by causing an aldonic acid or uronic acid to undergo intramolecular cyclodehydration) with an organopolysiloxane containing at least one aminoalkyl group to form an amide bond.

As the aminoalkyl group, an aminoalkyl group having 1 to 20 carbon atoms, especially an aminoalkyl group having 1 to 8 carbon atoms is preferred. Illustrative of the lactone compound formed as a result of intramolecular cyclodehydration of an aldonic acid or a uronic acid are lactones of aldonic acids derived from reducing monosaccharides such as D-glucose, D-galactose, D-allose, D-aldose, D-mannose, D-gulose, D-idose and D-talose; lactones of aldonic acids derived from reducing disaccharides such as maltose, cellobiose, lactose, xylobiose, isomaltose, nigerose and kojibiose; lactones of aldonic acids derived from reducing trisaccharides such as maltotriose, panose and isomaltotriose; lactones of aldonic acids derived from reducing oligosaccharides of tetrasaccharides and higher; and lactones of uronic acids such as D-glucuronic acid, L-iduronic acid and mannuronic acid. They can be provided for reaction either singly or as a mixture.

The reaction between the organopolysiloxane precursor having one or more aminoalkyl groups and the saccharide lactone can be achieved by using the saccharide lactone preferably in a molar amount 1.0 to 1.3 times as much as the amino groups in the organopolysiloxane precursor, mixing them in a solvent, and then stirring the resultant solution at a concentration of from 5 to 30 wt. % under heat and reflux for 3 to 20 hours. As the solvent employed in this reaction, a lower alcohol such as methanol, ethanol, 1-propanol or 2-propanol is suited.

Further, it is also possible to use a copolymer in which a poly(N-propylenecarbobetaine) formed of recurring units, which is represented by the following formula (2):

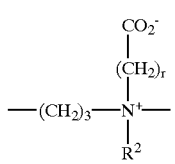

(2)

wherein $R^2$ represents a hydrogen atom, an alkyl group having 1 to 22 carbon atoms, a cycloalkyl group, an aralkyl group, an aryl group or an alkoxycarbonylalkyl group, and r stands for a value of from 1 to 5, is bonded to at least one terminal or side-chain silicon atom of an organopolysiloxane segment via a heteroatom-containing alkylene group.

In the above copolymer, the weight ratio of the organopolysiloxane segment to the poly(N-propylenecarbobetaine) segments may preferably range from 98/2 to 40/60 (more preferably 95/5 to 60/40), and the weight average molecular weight may preferably be from 1,000 to 500,000 (more preferably 5,000 to 300,000). If the weight ratio of the organopolysiloxane segment to the poly(N-propylenecarbobetaine) segments is greater than 98/2 or smaller than 40/60 or if the weight average molecular weight is lower than 1,000, the copolymer does not exhibit elasticity so that its emulsion stabilizing effects are insufficient. Such weight ratio and weight average molecular weight are therefore not preferred. On the other hand, a copolymer whose weight average molecular weight exceeds 500,000 is difficult to prepare.

Examples of the hetero-atom-containing alkylene group which intervenes the bonding between the organopolysiloxane segment and the poly(N-propylenecarbobetaine) segments include $C_{2-20}$ alkylene groups containing 1–3 nitrogen, oxygen and/or sulfur atoms. Their specific examples include:

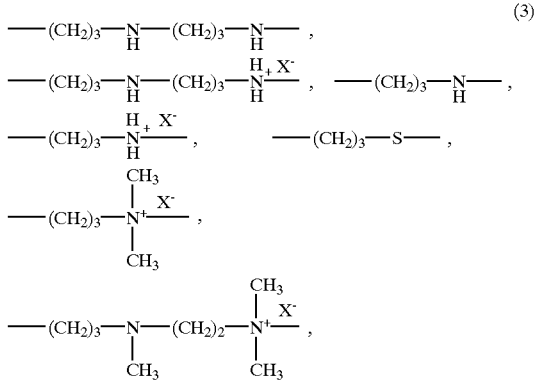

(3)

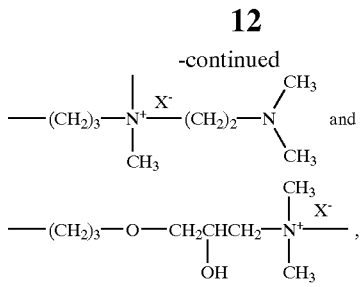

wherein $X^-$ represents a counter ion to a quaternary ammonium salt. On the other hand, illustrative of the cycloalkyl group are those having 3 to 6 carbon atoms, illustrative of the aralkyl group are phenylalkyl and naphthylalkyl, and illustrative of the aryl group are phenyl, naphthyl and alkyl-substituted phenyl.

To produce the above copolymer, the organopolysiloxane is first reacted with an end-reactive poly(N-propyleneimine) which has been obtained by subjecting to ring-opening polymerization a cyclic amine represented by the following formula (17):

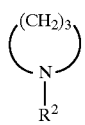

(17)

wherein $R^2$ has the same meaning as defined above, whereby an organopolysiloxane with the poly(N-propyleneimine) bonded thereto is prepared. Sodium chloroacetate and β-propiolactone, γ-butyrolatone or ε-caprolactone are reacted further to the above-prepared reaction product, whereby the organopolysiloxane with the poly(N-propylenecarbobetaine) bonded thereto is produced.

As another preparation process, the above-obtained organopolysiloxane with the poly(N-propyleneimine) bonded thereto is subjected to a quaternizing reaction with an $C_{1-22}$ alkyl halide, a cycloalkyl halide, an aryl halide or the like. Under basic conditions, a hydrolyzing reaction of the alkoxycarbonylethyl group or alkoxycarbonylmethyl group is then conducted, whereby the organopolysiloxane with the poly(N-propylenecarbobetaine) bonded thereto is produced.

Here, the ring-opening polymerization of the cyclic amine is carried out using as an initiator a compound such as a Lewis acid, protonic acid or an alkylating agent, for example, triethyleneoxonium tetrafluoroborate, benzyl chloride, benzyl bromide, benzyl iodide, methyl bromide, methyl iodide, ethyl bromide, ethyl iodide, dimethyl sulfate, diethyl sulfate, trifluoromethanesulfonic acid, methyl trifluoromethanesulfonate, ethyl trifluoromethanesulfonate, benzenesulfonic acid, methyl benzenesulfonate, ethyl benzenesulfonate, p-toluenesulfonic acid, methyl p-toluenesulfonate, or ethyl p-toluenesulfonate.

If an N-substituted azetidine is used as the cyclic amine, for example, a poly(N-substituted propylenecarbobetaine) is obtained.

Further, examples of solvents usable in the ring-opening polymerization of the cyclic amine and the production of the copolymer useful in the present invention include esters such as ethyl acetate and propyl acetate; ethers such as diethyl ether, diisopropyl ether, dioxane and tetrahydrofuran; ketones such as acetone and methyl ethyl ketone; halogen-containing solvents such as chloroform and methylene chloride; nitrile solvents such as acetonitrile and benzonitrile; and aprotonic polar solvents such as N,N-dimethylformamide, N,N-dimethylacetamide and dimethyl sulfoxide.

As a method for the connection of the poly(N-propyleneimine) chain and the silicone chain, the same method as that employed above for the connection between the poly(N-acylalkyleneimine) chain and the silicone chain can be used.

Japanese Patent Publication (Kokoku) No. SHO 63-16418 discloses betaine-containing siloxanes analogous to the above-described organopolysiloxane containing the poly(N-propylenecarbobetaine) bonded thereto and their preparation process. Effects for preventing separation of an emulsified, water-in-oil composition containing a lower alcohol (or, and also a silicone oil) are not referred to in its Examples.

As the high-molecular compound (B) having orientation to oil-water interfaces, a copolymer composed of the below-described three segments (i), (ii) and (iii) can also be used as a copolymer containing a hydrophilic segment and an organosiloxane segment because it prevents separation of an emulsified, water-in-oil composition containing a lower alcohol (or, and also a silicone oil) and exhibits emulsion stabilizing effects.

| (i) | at least one segment formed of a hydrophobic radical-polymerizable vinyl polymer | 1 to 98 wt. % |
|---|---|---|
| (ii) | at least one segment having hydrophilic polarity | 1.5 to 60 wt. % |
| (iii) | at least one segment formed of an organopolysiloxane | 0.1 to 90 wt. % |

Concerning the copolymer composed of the above segments (i), (ii) and (iii), analogous copolymers and their production processes are disclosed in Japanese Patent Application Laid-Open (Kokai) No. HEI 3-128311, Japanese Patent Application Laid-Open (Kokai) No. HEI 3-128312, WO95/06078, WO95/06079 and the like. The application fields of these copolymers however relates to hair cosmetic preparations, and they are concerned with neither effects for improving the emulsion stability of an emulsified, water-in-oil composition containing a lower alcohol (or, and also a silicone oil) nor skin cosmetic preparations containing such copolymers and capable of giving refreshed feeling. Further, these publications do not contain any disclosure about effects that these copolymers may show orientation to and around water droplets in an emulsified, water-in-oil emulsion containing a lower alcohol (or, and also a silicone oil), serve as protecting films for the water droplets, prevent separation of the water-in-oil emulsion product and improve its emulsion stability.

A description will hereinafter be made about the copolymer composed of the above-described segments (i), (ii) and (iii).

As segments having the hydrophilic polarity of the segment (ii), segments similar to the above-mentioned hydrophilic segments can be mentioned.

Illustrative of the segment (i) formed of the hydrophobic radical-polymerized vinyl polymer are those derived from one or more compounds represented by the following formula (5):

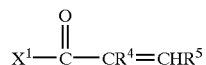

(5)

wherein $X^1$ represents a group selected from —OH, —NH$_2$, —OM (M: a cation), —OR$^3$, —NHR$^3$ or —N(R$^3$)$_2$ (R$^3$: a linear or branched alkyl group having 1 to 8 carbon atoms, N,N-dimethylaminoethyl, 2-hydroxyethyl, 2-methoxyethyl or 2-ethoxyethyl), and R$^4$ and R$^5$ represent an atom or group selected from a hydrogen atom, a linear or branched alkyl group having 1 to 8 carbon atoms, methoxy, ethoxy, 2-hydroxyethyl, 2-methoxyethyl or ethoxyethyl.

In the above formula (5), illustrative of the cation represented by M include Na$^+$, K$^+$, Mg$^{++}$, Ca$^{++}$, Zn$^{++}$, NH$_4^+$, alkylammonium, dialkylammonium, trialkylammonium and tetraalkylammonium.

Typical examples of the monomer making up the segment (i) include the acrylate esters of $C_1$–$C_8$ alcohols such as methanol, ethanol, methoxyethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-butanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol and 1-octadecanol; the methacrylate esters of such $C_1$–$C_8$ alcohols; styrene; polystyrene macromers; vinyl acetate; vinyl chloride; vinyl propionate; vinylidene chloride; α-methylstyrene; t-butylstyrene; butadiene; cyclohexadiene; ethylene; propylene; vinyltoluene; and mixtures thereof.

Preferred examples include n-butyl methacrylate, isobutyl methacrylate, 2-ethylhexyl methacrylate, methyl methacrylate, t-butyl methacrylate and mixtures thereof.

Illustrative of the segment (iii) derived from the organopolysiloxane is a segment derived from an organopolysiloxane represented by the following formula (6):

$$E(Y)_s Si(R^6)_{3-t}(Z^1)_t \quad (6)$$

wherein E represents a vinyl group copolymerizable with the segment (i) or (ii), Y represents a divalent connecting group, $R^6$ represents a hydrogen atom, lower alkyl group, aryl group or alkoxy group, $Z^1$ represents a monovalent siloxane polymer moiety having an average molecular weight of at least 500, s stands for 0 or 1, and t stands for an integer of 1 to 3. The weight average molecular weight of the organopolysiloxane (6) is preferably from about 1,000 to about 500,000 more preferably from about 5,000 to about 400,000, and notably from about 5,000 to about 300,000. Examples of the organopolysiloxane (6) include dimethylpolysiloxanes represented by the following formulas (7) to (12), respectively:

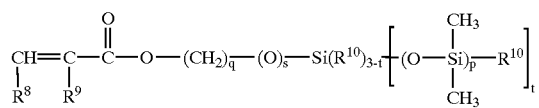

(7)

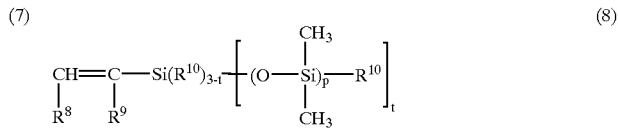

(8)

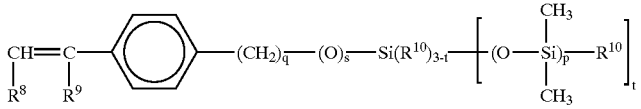

(9)

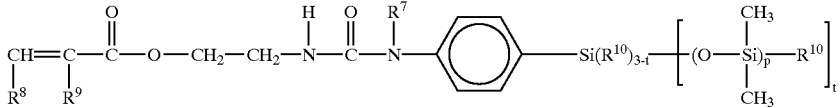

(10)

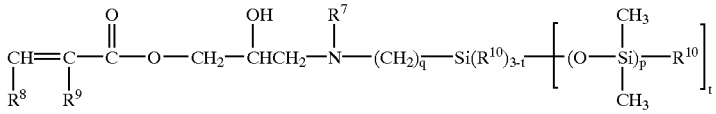

(11)

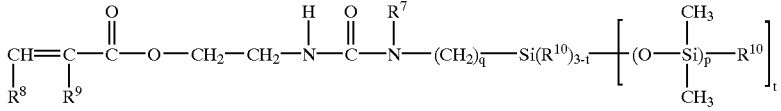

(12)

wherein $R^7$ represents a hydrogen atom or an alkyl group, $R^8$ represents a hydrogen atom or a carboxyl group (preferably a hydrogen atom), $R^9$ represents a hydrogen atom or a methyl or carboxylmethyl group (preferably a methyl group), $R^{10}$ represents an alkyl, alkoxy, alkylamino, aryl or hydroxyl group (preferably an alkyl group), q stands for an integer of from 2 to 6, p stands for an integer of from 5 to 700 (preferably about 250), s stands for 0 or 1, and t stands for an integer of from 1 to 3.

The copolymer composed of the segments (i), (ii) and (iii) can have the composition that the segment (i) accounts for 1 to 98 wt. % (preferably 1–90 wt. %, more preferably 50 to 90 wt. %), the segment (ii) accounts for 1.5 to 60 wt. % (preferably 7.5 to 50 wt. %), and the segment (iii) accounts for 0.1 to 90 wt. % (preferably 0.5 to 90 wt. %, more preferably 2 to 60 wt. %).

In the copolymer composed of the segments (i), (ii) and (iii), the segment (i) may preferably be one derived from a compound or compounds selected from t-butyl acrylate, t-butyl methacrylate or a mixture thereof, because the copolymer is soluble directly in cyclomethycone solvent.

As particularly preferred copolymers containing the segments (i), (ii) and (iii), the following copolymers can be mentioned (in the following description, each wt. % indicates the amount of the corresponding reactant added to the corresponding polymerization reaction and does not necessarily indicate its amount in the final polymer).

Acrylic acid/n-butyl methacrylate/polydimethylsiloxane (PDMS) macromer-molecular weight: 20,000 (10/70/20, V/V/V) (I)

N,N-dimethylacrylamide/isobutyl methacrylate/PDMS macromer-molecular weight: 20,000 (20/60/20, V/V/V) (II)

t-Butyl acrylate/t-butyl methacrylate/PDMS macromer-molecular weight: 10,000 (56/24/20 V/V/V) (III)

n-Butyl acrylate/2-methoxyethyl acrylate/poly(N-propionylethyleneimine)/polydimethylsiloxane 36/22/40/2 (IV)

n-Butyl acrylate/2-methoxyethyl acrylate/poly(N-propionylethyleneimine)/polydimethylsiloxane 33/22/40/5 (V)

n-Butyl acrylate/2-methoxyethyl acrylate/poly(N-propionylethyleneimine/polydimethylsiloxane 30.5/22/40/7.5 (VI)

n-Butyl acrylate/2-methoxyethyl acrylate/poly(N-propionylethyleneimine)/polydimethylsiloxane 28/22/40/10 (VII)

n-Butyl acrylate/2-methoxyethyl acrylate/poly(N-propionylethyleneimine)/polydimethylsiloxane 23/22/40/15 (VIII)

n-Butyl acrylate/poly(N-propionylethyleneimine)/polydimethylsiloxane 53/40/7 (IX)

n-Butyl acrylate/2-ethylhexyl methacrylate/poly(N-propionylethyleneimine)/polydimethylsiloxane 35/20/40/5 (X)

n-Butyl acrylate/2-methoxyethyl acrylate/poly(ethylene glycol)/polydimethylsiloxane 36/22/40/2 (XI)

The above-described copolymers containing the segments (i), (ii) and (iii) can all be synthesized by radical polymerization. Further, individual macromonomer can be polymerized in advance and can be formed finally into a copolymer. They can be synthesized by radical polymerization, for example, as will be described below.

Its general principal has been well ascertained (for example, see Odian: "Principles of Polymerization", 2nd. ed., pp. 178 and 318 (1981), John Wiley & Sons). Desired monomers and macromonomers are wholly placed in a reactor, together with a mutual solvent in an amount sufficient to provide the reaction mixture with an appropriate wiscosity when the reaction is completed. Typical monomer and macromonomer loadings are from about 20% to about 50%, on a weight basis. Undesired terminators, especially oxygen, can be removed as needed. This is done by evacuation or by purging with an inert gas, such as argon or nitroge. The initiator is introduced and the reaction brought to the temperature needed for initiation to occur, assuming thermal initiators are used. Nonlimiting examples of suitable initiators include those selected from the group consisting of azo initiators, peroxide initiators, redox initiators, and photochemical initiators. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as needed utilizing a variety of techniques including filtration, extraction, trituration, membrane separation, gel permeation chromatography, and like.

The high molecular compound (B) having orientation to oil-water interfaces emulsifies a system of an oil phase (which may contain a silicone oil in some instances), a lower alcohol and water, and forms a stably-emulsified, water-in-oil composition. The amount of the high molecular compound having orientation to the oil-water interfaces may be preferably from 0.05 to 10 wt. %, more preferably from 0.1 to 8 wt. %, and most preferably from 0.1 to 5 wt. %. In this range, a stably-emulsified, water-in-oil composition can be obtained. The viscosity of the oil phase as a continuous phase does not become high so that no sticking takes place at the time of use. The feeling of use is therefore good.

No particular limitation is imposed on the lower alcohol as the component (C) in the present invention. Preferred is however a lower alcohol which contains one or more hydroxyl groups in a molecule, has a low molecular weight and is soluble in water. Illustrative Of the lower alcohol are ethyl alcohol, propyl alcohol and isopropyl alcohol. It is preferred to incorporate such a lower alcohol in a proportion of preferably from 1 to 40 wt. %, more preferably from 2 to 30 wt. %, notably from 5 to 20 wt. % in the emulsified, water-in-oil composition or the skin cosmetic preparation containing same, because the stability is not lowered while making it possible to retain the ability to give refreshed feeling.

No particular limitation is imposed on water which is employed as the component (D) in the present invention. High-purity water such as purified water or deionized water is preferred. The amount of water may range preferably from 1 to 90 wt. %, more preferably from 3 to 85 wt. %, notably from 5 to 80 wt. % based on the emulsified, water-in-oil composition or the skin cosmetic preparation containing same.

In the emulsified, water-in-oil composition or the skin cosmetic preparation containing same, both pertaining to the present invention, the ratio of an outer phase (oil phase) to an inner phase (water phase) may preferably range from 10:1 to 1:10 (inner phase:outer phase), with 8:1 to 1:8 being particularly preferred. Further, the mixing ratio of water to a lower alcohol, which are both incorporated in the inner phase, may preferably range from 50:1 to 1:5, with 10:1 to 1:3 being particularly preferred.

In addition to the above-described essential components, the emulsified, water-in-oil composition and the skin cosmetic composition, which pertain to the present invention, can contain components which may be added to conventional cosmetic preparations as needed. As water phase components, it is possible to add a moisturizing agent such as propylene glycol, dipropylene glycol, 1,3-butylene glycol, glycerin, maltitol, sorbitol, polyethylene glycol, sodium hyaluronate or a pyrrolidone carboxylate salt, a intercellular lipid (ceramide or the like), a coloring matter such as an inorganic pigment or an organic pigment, a surfactant such as a cationic-surfactant, an anionic surfactant or a nonionic surfactant, a medicine such as vitamin E or vitamin E acetate, an astringent, an antioxidant, a preservative, a perfume, a pH regulator such as citric acid, sodium citrate, lactic acid, sodium lactate or sodium secondary phosphate, inorganic salt such as magnesium sulfate or sodium chloride, a thickening agent such as montmorillonite modified with an organic substance, an ultraviolet absorber and/or the like to the emulsified, water-in-oil composition and the skin cosmetic composition, which pertain to the present invention, as needed.

The skin cosmetic preparation according to the present invention can be produced as a cream, a lotion, a foundation, a lip stick or the like by a method known per se in the art.

The present invention will hereinafter be described further based on the following Examples. It should however be borne in mind that the present invention is not limited to the Examples. Unless otherwise specifically indicated, the designations of "%" in the Examples are all by weight basis. In Synthesis Examples, each weight average molecular weight is a value determined by gel permeation liquid chromatography while using chloroform as a developer solvent, and the value is an equivalent polystyrene value.

Synthesis Example 1

Synthesis of poly(N-acetylethyleneimine)-modified Silicone

A mixture of 13.03 g (0.070 mole) of methyl p-toluene sulfonate (methyl tosylate), 70 g (0.82 mole) of 2-methyl-2-oxazoline, 10 ml of acetonitrile and 30 ml of chloroform was refluxed for 6 hours, whereby an end-reactive polymer (molecular weight: 1,000) of poly(N-acetylethyleneimine) was synthesized. To the reaction mixture, a solution of 31.8 g of polydimethylsiloxane substituted by 3-aminopropyl groups at both ends thereof ("FM3311", trade name; product of Chisso Corporation; molecular weight: 1,000) in 50 ml of chloroform was added, followed by a reaction at 55° C. for 24 hours. The solvent was distilled off under reduced pressure, whereby a block copolymer (molecular weight: 3,000) with poly(N-acetylethyleneimine) chains bonded to the both ends of the polydimethylsiloxane, respectively, was obtained. This copolymer was a brittle solid of a pale yellow color [yield: 110.2 g (96%)].

Synthesis Example 2

Synthesis of poly(N-n-dodecanoylpropyleneimine)-modified Silicone

A mixture of 1.45 g ($7.8 \times 10^{-3}$ mole) of methyl tosylate, 7.8 g (0.033 mole) of 2-n-undecyl-2-oxazine and 10 ml of dimethylacetamide was maintained at 100° C. for 24 hours, whereby poly(N-n-dodecanoylpropyleneimine) (molecular weight: 1,000) was synthesized. To the reaction mixture, a solution of 38.9 g of polydimethylsiloxane substituted by 3-aminopropyl groups at both ends thereof ("FM3325", trade name; product of Chisso Corporation; molecular weight: 10,000) in 50 ml of chloroform was added, followed by reflux for 72 hours. The reaction mixture was then reprecipitated with methanol and the residue was dried under reduced pressure. The thus-obtained polymer was a viscous liquid of a yellow color and its molecular weight was 12,000 [yield: 45.7 g (95%)].

Synthesis Example 3

Synthesis of poly(N-acetylethyleneimine)-modified Silicone

A mixture of 3.26 g (0.018 mole) of methyl tosylate, 70 g (0.82 mole) of 2-methyl-2-oxazoline, 10 ml of acetonitrile and 40 ml of chloroform was refluxed for 6 hours, whereby poly(N-acetylethyleneimine) (molecular weight: 4,000) was synthesized. To the reaction mixture, a solution of 63.6 g of polydimethylsiloxane substituted by 3-aminopropyl groups at side chains thereof ("KF865", trade name; product of Shin-Etsu Chemical Co., Ltd.; amine equivalent: 4,400; molecular weight: 2,000) in 150 ml of chloroform was added, followed by a reaction at 55° C. for 24 hours. The solvent was distilled off under reduced pressure, whereby a mixture of a graft polymer (molecular weight: 6,000) with poly(n-acetylethyleneimine) chains bonded to the polydimethylsiloxane and a silicone having a molecular weight of 2,000 was formed. This polymer was a brittle solid of a pale yellow color [yield: 134.1 g (98%)].

Synthesis Example 4

Synthesis of Silicone Modified with a Random Copolymer of N-acetylethyleneimine and N-n-octanoylethyleneimine A mixture of 1.86 g (0.01 mole) of methyl tosylate, 10 g (0.059 mole) of 2-n-heptyl-2-oxazoline, 10 g (0.1174 mole) of 2-methyl-2-oxazoline and 20 ml of chloroform was refluxed for 6 hours, whereby an N-acetylethyleneimine-N-n-octanoylethyleneimine random copolymer (molecular weight: 2,000) was synthesized.

To a solution of 43.34 g of polydimethylsiloxane with 2-aminoethylaminopropyl groups substituted to side chains ["KF857", trade name; product of Shin-Etsu Chemical Co., Ltd.; amine equivalent: 830; viscosity: 70 cs (25° C.)] in 150 g of chloroform, the above-synthesized random copolymer solution was added, followed by reflux for 10 hours. The solvent was distilled off under reduced pressure, whereby a copolymer (molecular weight: 19,000) with poly(N-acylethyleneimine) grafted on the polydimethylsiloxane was obtained. This copolymer was a viscous liquid of a pale yellow color [yield: 64.5 g (99%)].

Synthesis Example 5

Synthesis of poly(N-formylpropyleneimine)-modified Silicone

A mixture of 13.03 g (0.070 mole) of methyl tosylate, 70 g (0.82 mole) of 2-oxazine, 10 ml of acetonitrile and 30 ml of chloroform was refluxed for 6 hours, whereby an end-reactive polymer (molecular weight: 1,000) of poly(N-formylpropyleneimine) was synthesized. To the reaction mixture, a solution of 50 g of polydimethylsiloxane with 3-mercaptopropyl groups substituted to side chains ["X-22-980", trade name; product of Shin-Etsu Chemical Co., Ltd.; sulfur content: 1.7%; viscosity: 150 cs (25° C.)] in 100 ml of chloroform was added, followed by a reaction at 30° C. for 3 hours and then at 60° C. for 24 hours. The solvent was distilled off under reduced pressure, whereby a graft polymer (molecular weight: 6,200) with poly(N-formylpropyleneimine) chains bonded to the polydimethylsiloxane was obtained. This copolymer was a viscous liquid of a pale yellow color [yield: 129 g (97%)].

Synthesis Example 6

Synthesis of Amino-modified Silicone Containing Tertiary Amino Groups in Side Chains (Precursor for Synthesis Example 7)

After a mixture of 6.00 g (0.031 mole) of N,N-dimethylaminopropylmethyldimethoxysilane and 1.46 g (0.081 mole) of water was heated at 60° C. for 5 hours, the resulting methanol and water were distilled off at 60° C. under reduced pressure of 2 to 5 mmHg. The reaction mixture was heated to 80° C. and was then added with 228 g (0.769 mole) of octamethylcyclotetrasiloxane, 1.92 g (1.18×10$^{-2}$ mole) of hexamethyldisiloxane and 0.90 g of a polymerization catalyst [which contained 0.12 g (1.32×10$^{-3}$ mole) of tetramethylammonium hydroxide and had been prepared by dissolving tetramethylammonium hydroxide pentahydrate in octamethylcyclotetrasiloxane and toluene, conducting a reaction at 80° C. for 12 hours and then drying the reaction product at 80° C. in a vacuum of 2 mmHg; the content of tetramethylammonium hydroxide was determined by the hydrochloric acid titration method]. The thus-obtained mixture was heated for 72 hours under a nitrogen gas atmosphere. By removing an oligomer at 120° C. in a vacuum of 2 to 5 mmHg, an amino-modified silicone containing tertiary amino groups in side chains and represented by the below-described formula was synthesized. The reaction product was a colorless clear oil (225 g). Its average molecular weight was 22,000. Its amine equivalent was determined to be 7,200 by the hydrochloric acid titration method.

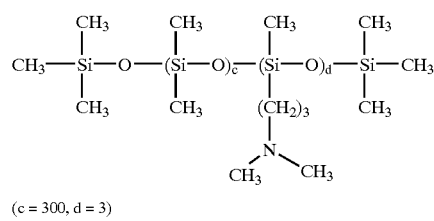

(c = 300, d = 3)

Synthesis Example 7

Synthesis of poly(N-propionylethyleneimine)-modified Silicone

Diethyl sulfate (2.36 g; 0.0153 mole) and 2-ethyl-2-oxazoline (30.3 g; 0.306 mole) were dissolved in 43 ml of chloroform. The resultant solution was heated under reflux for 5 hours under a nitrogen gas atmosphere, whereby an end-reactive polymer (molecular weight: 2,000) of poly(N-propionylethyleneimine) was synthesized. To the reaction mixture, a solution of 100 g (0.0139 mole in terms of amino groups) of the tertiary-amino-modified silicone synthesized in Synthesis Example 6 in 270 ml of chloroform was added at once, followed by heating under reflux for 16 hours. The reaction mixture was concentrated under reduced pressure, whereby a graft copolymer (molecular weight: 28,900) with N-propionylethyleneimine chains bonded to the polydimethylsiloxane, said copolymer being represented by the below-described formula, was obtained. This polymer was a rubbery solid of a pale yellow color [yield: 129 g (97%)].

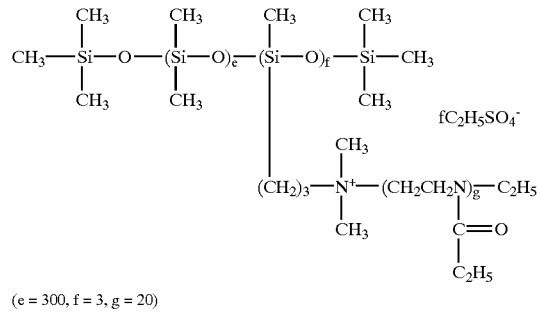

(e = 300, f = 3, g = 20)

Synthesis Example 8

Synthesis of poly(N-propionylethyleneimine)-modified Silicone

Diethyl sulfate (3.55 g; 0.0230 mole) and 2-ethyl-2-oxazoline (27.4 g; 0.276 mole) were dissolved in 60 g of dried ethyl acetate. The resultant solution was heated under reflux for 4 hours under a nitrogen gas atmosphere, whereby an end-reactive polymer (molecular weight: 1,200) of poly (N-propionylethyleneimine) was synthesized. To the reaction mixture, a 50% ethyl acetate solution of 400 g (0.0192 mole in terms of amino groups) of polydimethylsiloxane with side chains modified with primary aminopropyl groups, respectively (molecular weight: 110,000; amine equivalent: 20,800) was added at once, followed by heating under reflux for 8 hours. The reaction mixture was concentrated under reduced pressure, whereby a graft copolymer (molecular weight: 15,000) with N-propionylethyleneimine chains bonded to the polydimethylsiloxane was obtained. This copolymer was a rubbery solid of a pale yellow color [yield: 427 g (99%)].

Synthesis Example 9

Synthesis of poly(N-propionylethyleneimine)-modified Silicone

Diethyl sulfate (3.77 g; 0.0244 mole) and 2-ethyl-2-oxazoline (48.4 g; 0.488 mole) were dissolved in 107 g of dried chloroform. The resultant solution was heated under reflux for 5 hours under a nitrogen gas atmosphere, whereby an end-reactive polymer (molecular weight: 2,000) of poly (N-propionylethyleneimine) was synthesized. To the reaction mixture, a 50% ethyl acetate solution of 400 g (0.0407 mole in terms of amino groups) of polydimethylsiloxane with side chains modified with primary aminopropyl groups, respectively (molecular weight: 110,000; amine equivalent: 9,840) was added at once, followed by heating under reflux for 13 hours. The reaction mixture was concentrated under reduced pressure, whereby a graft copolymer (molecular weight: 137,000) with N-propionylethyleneimine chains bonded to the polydimethylsiloxane was obtained. The thus-obtained copolymer was a rubbery solid of a pale yellow color [yield: 444 g (98%)].

Synthesis Example 10

Synthesis of alkylpyrrolidone-modified Silicone

Five hundred grams of methylhydrogenpolysiloxane (2.91 moles in terms of SiH; weight average molecular weight: 100,000; SiH equivalent: 172) were added with 2.0 g of a 5% isopropyl alcohol solution of chloroplatinic acid. While stirring the resultant mixture under a nitrogen gas atmosphere, 382 g (3.06 moles) of N-(3-propenyl) pyrrolidone were added dropwise at such a rate as keeping the internal temperature of the system below 60° C. After completion of the dropwise addition, the internal temperature of the system was maintained at 65° C., at which stirring was continued for further 3 hours. The temperature of the reaction mixture was then allowed to cool down to room temperature. The reaction mixture was added with 3,530 g of ethanol to from a homogeneous solution. Ten grams of activated carbon powder were added further, followed by stirring for 30 minutes at room temperature. The activated carbon was then filtered off. The thus-obtained solution was concentrated under reduced pressure to distill off ethanol and unreacted N-(3-propenyl)pyrrolidone, whereby 847 g of methylpolysiloxane with alkylpyrrolidone groups in side chains were obtained as a colorless transparent rubbery solid (yield: 98%). The weight average molecular weight was 155,000. Further, no absorption corresponding to Si—H stretching vibrations (2125 cm$^{-1}$) was observed in a FT-IR spectrum.

Synthesis Example 11

Synthesis of Silicone Containing saccharide-derived Residual Groups

Mixed were 200 g (0.201 mole in terms of amino groups) of γ-aminopropyl-modified dimethylpolysiloxane having an amine equivalent of 996 and a weight average molecular weight of 108,000, 39.3 g (0.221 mole) of δ-gluconic lactone and 200 g of methanol. The resultant mixture was heated for 8 hours under reflux while vigorously stirring it under a nitrogen gas atmosphere. The thus-obtained solution was diluted threefold in methanol, and was then added dropwise to 10 liters of water which was under vigorous stirring at room temperature. The stirring was stopped and the precipitate was collected by filtration. The precipitate was washed with water and then dried, whereby dimethylpolysiloxane containing saccharide-derived residual groups was obtained as a colorless transparent elastic solid in an amount of 204 g (yield: 86%). As a result of neutralization titration by hydrochloric acid in which methanol was used as a solvent, no amino group was found to remain. Further, the content of the silicone segment was 86%.

Synthesis Example 12

Synthesis of carbobetaine-modified Silicone

Diethyl sulfate (30.6 g; 0.198 mole) and 1-(2-carboethoxyethyl)azetidine (1498.2 g; 9.53 moles) were dissolved in 3,058 g of dried ethyl acetate. The resultant solution was heated under reflux for 15 hours under a nitrogen gas atmosphere, whereby an end-reactive poly(N-propyleneimine) was synthesized. To the reaction mixture, a 50% ethyl acetate solution of 800 g (0.165 mole in terms of amino groups) of polydimethylsiloxane whose side chains had been modified with aminopropyl groups, respectively (molecular weight: 110,000, amine equivalent: 4,840) was added at once, followed by heating under reflux for 12 hours. The reaction mixture was concentrated under reduced pressure, whereby an N-propyleneimine-dimethylsiloxane copolymer was obtained as a pale yellow solid [yield: 2,212 g (95%)]. The thus-obtained reaction mixture was dissolved in 5,000 g of diethyl ether, to which 824 g (11.4 moles) of β-propiolactone were added at room temperature. The thus-obtained mixture was reacted for 24 hours at room temperature. The resultant solution was concentrated under reduced pressure, whereby an N-propylenecarbobetaine-dimethylsiloxane copolymer was obtained as a pale yellow solid.

Synthesis Example 13

Synthesis of poly(2-ethyl-2-oxazoline) Macromonomer whose Terminals were Blocked with Vinyl-benzyl Groups (Precursor for Synthesis Example 14)

A mixture of 50 g (0.5044 mole) of 2-ethyl-2-oxazoline, 0.3816 g (0.0025 mole) of m,p-vinylbenzyl chloride (product of Aldrich Chemical Co., Inc.), 0.562 g (0.0037 mole) of sodium iodide, 0.06 g (0.00023 mole) of N,N'-diphenyl-p-phenylenediamine and 50 ml of acetonitrile was refluxed for 16 hours at 90° C. Dichloromethane (100 ml) was added to terminate the reaction. A reaction mixture containing the synthesized product was filtered and was then caused to precipitate in 800 ml of ethyl ether. The precipitate was collected by suction filtration and then dried in a vacuum, whereby a poly(2-ethyl-2-oxazoline) macromonomer was obtained [yield: 40 g (90%)].

Synthesis Example 14

Synthesis of n-butyl acrylate/2-methoxyethyl acrylate/poly(N-propionylethyleneimine)/ polydimethylsiloxane Copolymer (36/22/40/5)

To a mixture of 3.6 g (0.0281 mole) of n-butyl acrylate, 2.2 g (0.0169 mole) of 2-methoxyethyl acrylate, 0.2 g (0.00002 mole) of dimethylpolysiloxane (molecular weight: 10,000; product of Chisso Corporation), 4.0 g (0.001 mole) of the poly(2-ethyl-2-oxazoline) macromonomer prepared in Synthesis Example 13 and 90 ml of acetone, 0.015 g (0.0001 mole) of azobisisobutyronitrile (AIBN) was added as an initiator, followed by refluxing for 24 hours. Methanol (5 ml) was added to terminate the synthesis. The reaction mixture was charged in a Teflon-coated pan and placed in a vacuum drier. At room temperature, acetone was allowed to evaporate. The thus-obtained synthesized product was dissolved in ethanol, any insoluble matter was filtered off, and the filtrate was taken out. Ethanol was distilled off under reduced pressure, whereby an n-butyl acrylate/2-methoxyethyl acrylate/poly(N-propionylethyleneimine)/polydimethylsiloxane copolymer was obtained. This copolymer was a rubbery solid (yield: 9.0 g).

Synthesis Example 15

Synthesis of Acrylic Acid/n-butyl methacrylate/polydimethylsiloxane Copolymer (10/70/20)

Polymer I: Placed in a flask were 10 parts of acrylic acid, 70 parts of n-butyl methacrylate and 20 parts of 20K PDMS macromer. Ethyl acetate was added in an amount sufficient to give a 40% final monomer concentration. Benzoyl peroxide, an initiator, was added to a concentration of 0.1 wt. % based on the amount of the monomers. The vessel was evacuated and filled again with nitrogen. The reaction system was heated to 60° C., which was then maintained under stirring for 48 hours. The reaction system was then cooled to room temperature, whereby the reaction was terminated. The reaction mixture was charged in a Teflon-coated pan and placed in a vacuum oven. Ethyl acetate was allowed to evaporate, whereby an acrylic acid/n-butyl methacrylate/polydimethylsiloxane (10/70/20) copolymer (molecular weight: 100,000) was obtained.

EXAMPLES 1 to 15

Comparative Examples 1 to 5

In each of the Examples and Comparative Examples, an emulsified, water-in-oil composition (skin cosmetic preparation) of the corresponding composition shown in Table 1 or 2 was produced by the below-described procedures. It was evaluated with respect to emulsion storage stability, refreshed feeling and stick-free property. The results are shown in Table 1 or 2.
(Production Procedures)
Components (1) to (14) were combined, to which a mixture of components (15) to (17) was slowly added under stirring over 30 minutes. The resultant mixture as agitated further for 10 minutes in a homomixer, so that the mixture was emulsified. The mixture was defoamed and filled in a polyethylene container, whereby a lotion was prepared.
(Evaluation Methods)
(1) Emulsion Storage Stability About 70 g portions of each emulsion product were filled in 100-ml polyethylene containers and then stored for 1 month at 5° C., room temperature (20–25° C.) and 40° C., respectively. The stability of the emulsion product in each container was determined from its external appearance in accordance with the following standard:

A: no change.
B: occurrence of irregularity in the surface.
C: separation of a liquid to a thickness not greater than 1 mm in the surface.
D: complete separation (1 mm or thicker)
(2) Refreshed Feeling By 15 expert panelers, each emulsified cosmetic preparation of the water-in-oil type was applied on their faces. The emulsified cosmetic preparation was evaluated in accordance with the following standards. The refreshed feeling was evaluated in accordance with the following standard and ranked based on its average score.

| | |
|---|---|
| Poor | score 1 |
| Slightly poor | score 2 |
| Average | score 3 |
| Slightly good | score 4 |
| Good | score 5. |

(3) Stick-free Property
In a similar manner as the above-described evaluation of the refreshed feeling (2), the stick-free property was determined based on its average score.

| | |
|---|---|
| Poor | score 1 |
| Slightly poor | score 2 |
| Average | score 3 |
| Slightly good | score 4 |
| Good | score 5. |
| (Ranking standard) | |
| 4.5 ≦ average score ≦ 5 | A |
| 3.5 ≦ average score ≦ 4.5 | B |
| 2.5 ≦ average score ≦ 3.5 | C |
| 1.5 ≦ average score ≦ 2.5 | D |
| 1.0 ≦ average score ≦ 1.5 | E |

TABLE 1

| Components | Example |||||||||||
|---|---|---|---|---|---|---|---|---|---|---|---|
| | 1 | 2 | 3 | 4 | 5 | 6 | 7 | 8 | 9 | 10 | 11 |
| (1) Poly(N-acetylethyleneimine)-modified silicone (Syn. Ex. 1) | 5 | | | | | | | | | | |
| (2) Poly(N-n-dodecanoylpropyleneimine)-modified silicone (Syn. Ex. 2) | | 5 | | | | | | | | | |
| (3) Poly(N-acetylethyleneimine)-modified solicone (Syn. Ex. 3) | | | 5 | | | | | | | | |
| (4) Silicone modified with poly(N-acetylethyleneimine)-(N-n-octanoylethyleneimine) random copolymer (Syn. Ex. 4) | | | | 5 | | | | | 1 | 3 | 10 |
| (5) Poly(N-formylpropyleneimine)-modified silicone (Syn. Ex. 5) | | | | | 5 | | | | | | |
| (6) Poly(N-propionylethyleneimine)-modified silicone (Syn. Ex. 7) | | | | | | 5 | | | | | |
| (7) Poly(N-propionylethyleneimine)-modified silicone (Syn. Ex. 8) | | | | | | | 5 | | | | |
| (8) Poly(N-propionylethyleneimine)-modified silicone (Syn. Ex. 9) | | | | | | | | 5 | | | |
| (9) Glyceryl monooleate | | | | | | | | | | | |

TABLE 1-continued

| Components | Example | | | | | | | | | | |
|---|---|---|---|---|---|---|---|---|---|---|---|
| | 1 | 2 | 3 | 4 | 5 | 6 | 7 | 8 | 9 | 10 | 11 |
| (10) Sorbitan diisostearate | | | | | | | | | | 2 | |
| (11) Dimethylsiloxane-methylpolyoxyethylenesiloxane copolymer ("KF6017", trade name; product of Shin-Etsu Chemical Co., Ltd.) | | | | | | | | | 4 | | |
| (12) Octamethylcyclotetrasiloxane | 20 | 20 | 20 | 20 | 20 | 20 | 20 | 20 | 20 | 20 | 20 |
| (13) Dimethylpolysiloxane (6 cs) | 10 | 10 | 10 | 10 | 10 | 10 | 10 | 10 | 10 | 10 | 10 |
| (14) Squalane | 10 | 10 | 10 | 10 | 10 | 10 | 10 | 10 | 10 | 10 | 10 |
| (15) Ethanol | 10 | 10 | 10 | 10 | 10 | 10 | 10 | 10 | 10 | 10 | 10 |
| (16) Purified water | 40 | 40 | 40 | 40 | 40 | 40 | 40 | 40 | 40 | 40 | 35 |
| (17) Glycerin | 5 | 5 | 5 | 5 | 5 | 5 | 5 | 5 | 5 | 5 | 5 |
| Results of evaluation | | | | | | | | | | | |
| Stability | | | | | | | | | | | |
| 5° C., 1 month later | A | A | A | A | A | A | A | A | A | A | A |
| Room temperature, 1 month later | A | A | A | A | A | A | A | A | A | A | A |
| 40° C., 1 month later | A | A | A | A | A | A | A | A | A | A | A |
| Feeling of use | | | | | | | | | | | |
| Refreshed feeling | A | A | A | A | A | A | A | A | A | A | A |
| Stick-free feeling | A | A | A | A | A | A | A | A | A | A | A |

TABLE 2

| Components | Example | | | | Comparative Example | | | | |
|---|---|---|---|---|---|---|---|---|---|
| | 12 | 13 | 14 | 15 | 1 | 2 | 3 | 4 | 5 |
| (1) Poly(N-acetylethyleneimine)-modified silicone (Syn. Ex. 1) | | | | | | | | | |
| (2) Poly(N-n-dodecanoylpropyleneimine)-modified silicone (Syn. Ex. 2) | | | | | | | | | |
| (3) Poly(N-acetylethyleneimine)-modified solicone (Syn. Ex. 3) | | | | | | | | | |
| (4) Silicone modified with poly(N-acetylethyleneimine)-(N-n-octanoylethyleneimine) random copolymer (Syn. Ex. 4) | | | | | | | | | 5 |
| (5) Poly(N-formylpropyleneimine)-modified silicone (Syn. Ex. 5) | | | | | | | | | |
| (6) Poly(N-propionylethyleneimine)-modified silicone (Syn. Ex. 7) | | | | | | | | | |
| (7) Poly(N-propionylethyleneimine)-modified silicone (Syn. Ex. 8) | | | | | | | | | |
| (8) Poly(N-propionylethyleneimine)-modified silicone (Syn. Ex. 9) | 5 | 5 | 5 | 5 | | | | | |
| (9) Glyceryl monooleate | | | | | 5 | | | | |
| (10) Sorbitan diisostearate | | | | | | 5 | | | |
| (11) Dimethylsiloxane-methylpolyoxyethylenesiloxane copolymer ("KF6017", trade name; product of Shin-Etsu Chemical Co., Ltd.) | | | | | | | 5 | 5 | |
| (12) Octamethylcyclotetrasiloxane | 25 | 30 | 20 | 20 | 20 | 20 | 20 | 20 | 20 |
| (13) Dimethlpolysiloxane (6 cs) | 15 | 20 | 10 | 10 | 10 | 10 | 10 | 10 | 10 |
| (14) Squalane | | | 10 | 10 | 10 | 10 | 10 | 10 | 10 |
| (15) Ethanol | 10 | 10 | 5 | 20 | 10 | 10 | 10 | | |
| (16) Purified water | 40 | 30 | 45 | 30 | 40 | 40 | 40 | 50 | 50 |
| (17) Glycerin | 5 | 5 | 5 | 5 | 5 | 5 | 5 | 5 | 5 |
| Results of evaluation | | | | | | | | | |
| Stability | | | | | | | | | |
| 5° C., 1 month later | A | A | A | A | D | D | D | B | A |
| Room temperature, 1 month later | A | A | A | A | D | D | D | C | A |
| 40° C., 1 month later | A | A | A | A | D | D | D | D | A |
| Feeling of use | | | | | | | | | |
| Refreshed feeling | A | A | A | A | A | A | A | D | D |
| Stick-free feeling | A | A | A | A | A | A | A | C | C |

From Table 1 and Table 2, the emulsified, water-in-oil cosmetic preparations according to the present invention, which were each added with the corresponding high molecular compound having orientation to oil-water interfaces and the corresponding lower alcohol (Examples 1 to 15), were excellent in storage stability at the respective temperature conditions and as feeling of use, gave excellent refreshed feeling and stick-free feeling. On the other hand, the emulsified, water-in-oil cosmetic preparations, which contained neither high molecular compound having orientation to oil-water interfaces nor a lower alcohol (Comparative Examples 1 to 3), were excellent in refreshed feeling and were stick-free as feeling of use, but were inferior in storage stability. The emulsified, water-in-oil cosmetic preparations, which were not added with ethanol, i.e., a lower alcohol (Comparative Examples 4 to 5), tended to show better stability, in particular, the emulsified, water-in-oil cosmetic preparation added with the high molecular compound having orientation to oil-water interfaces (Comparative Example 5) was excellent in storage stability, but in the feeling of use, they were inferior in refreshed feeling and had stickiness.

EXAMPLE 16

Emulsified, Creamy Cosmetic Preparation

| (1) | Dimethylpolysiloxane (viscosity 2 cs) | 10% |
|---|---|---|
| (2) | Decamethylcyclopentasiloxane | 10% |
| (3) | Perfluoropolyether ("FOMBLIN HC-04", trade name; product of AUSIMONT K.K.) | 10% |
| (4) | Squalane | 5% |
| (5) | Lanolin | 1% |
| (6) | Poly(N-propionylethyleneimine)-modified silicone (Synthesis Example 7) | 3% |
| (7) | Purified water | Balance |
| (8) | 95% ethanol | 15% |
| (9) | 1,3-butylene glycol | 5% |
| (10) | Sodium hyaluronate | 0.1% |
| | | 100% |

The above components (1) to (6) were combined, to which a mixture of the above components (7) to (10) was slowly added under stirring over 30 minutes. The resultant mixture was then stirred and emulsified for 10 minutes in a homomixer. The thus-formed emulsion was defoamed and filled in polyethylene containers, so that an emulsified, creamy cosmetic preparation was formulated.

EXAMPLE 17

Creamy Foundation (Components)

| (1) | Isoparaffin (C$_{10}$–C$_{12}$) | 15% |
|---|---|---|
| (2) | Octamethylcyclotetrasiloxane | 8% |
| (3) | Dimethylpolysiloxane (viscosity 6 cs) | 7% |
| (4) | Cetanol | 1% |
| (5) | Diisostearyl malate | 6% |
| (6) | Zinc distearate | 1% |
| (7) | Monoisostearyl glyceryl ether | 1% |
| (8) | Dimethylsiloxane-methylpolyoxyethylenesiloxane copolymer | 1% |
| (9) | Poly(N-propionylethyleneimine)-modified silicone (Synthesis Example 8) | 2% |
| (10) | Silicone-treated, fine particulate titanium oxide* (product of Tayka Corporation | 5% |
| (11) | Silicone-treated, spherical silica* | 1% |
| (12) | Silicone-treated titanium oxide* | 5% |
| (13) | Silicone-treated, iron oxides (red, yellow, black)* | 3% |
| (14) | Glycerin | 3% |
| (15) | 95% ethanol | 3% |
| (16) | Methylparaben | 0.1% |
| (10) | Water | Balance |
| | | 100% |

*surface-treated to 2% with methylhydrogenpolysiloxane.

The components (1) to (9) were heated and mixed at 80° C. Separately, the components (10) to (13) were mixed in a Henschel mixer and then added to the premixed components (1) to (9). The resultant mixture was dispersed and mixed in a mixer. To the resultant mixture, a mixture of the component (14) to (16) which had been to 40° C. was slowly added under stirring over 30 minutes, followed by further stirring for 10 minutes in a homomixer to emulsify same. The thus-formed emulsion was slowly cooled to room temperature under stirring, defoamed and then filled in bottles, so that a creamy foundation was formulated.

EXAMPLE 18

Sunscreen Lotion

| (1) | Octamethylcyclotetrasiloxane | 3% |
|---|---|---|
| (2) | Decamethylcyclopentasiloxane | 10% |
| (3) | Dimethylpolysiloxane (viscosity 1 cs) | 3% |
| (4) | Octyldodecyl myristate | 8% |
| (5) | Stearic acid | 0.5% |
| (6) | Octyl methoxycinnamate | 2% |
| (7) | Poly(N-propionylethyleneimine)-modified silicone (Synthesis Example 8) | 5% |
| (8) | Silicone-treated, fine particulate titanium oxide** (product of Tayka Corporation | 3% |
| (9) | Silicone-treated, fine particulate zinc oxide*** (product of Sakai Chemical Industry Co., Ltd.) | 5% |
| (10) | Nylon powder | 2% |
| (11) | 95% ethanol | 8% |
| (12) | Sodium citrate | 0.5% |
| (13) | Glycerin | 3% |
| (14) | Magnesium sulfate | 1% |
| (15) | Water | Balance |
| | | 100% |

**surface-treated to 5% with methylhydrogenpolysiloxane.
***Finely-divided zinc white silicone-treated to an amount of 2%.

The components (1) to (10) were heated and mixed at 70° C. Separately, the components (11) to (15) which had been heated and mixed beforehand at 40° C. were slowly added under stirring over 30 minutes, followed by further stirring for 10 minutes in a homomixer. The thus-formed emulsion was slowly cooled to room temperature under stirring, defoamed and then filled in bottles, so that a sunscreen lotion was formulated.

EXAMPLE 19

Liquid Foundation

| (1) | Octamethylcyclotetrasiloxane | 15% |
|---|---|---|
| (2) | Dimethylpolysiloxane (viscosity 2 cs) | 8% |
| (3) | octyl methoxycinnamate | 2% |
| (4) | 12-hydroxystearic acid | 1% |
| (5) | Octyldodecyl myristate | 7% |
| (6) | Dimethylsiloxane-methylpolyoxyethylenesiloxane copolymer | 3% |
| (7) | Poly(N-propionylethyleneimine)-modified silicone (Synthesis Example 9) | 0.5% |
| (8) | Silicone-treated, fine particulate titanium oxide* (product of Tayka Corporation | 7% |
| (9) | Spherical silicone resin powder ("TOSPEARL 120", trade name; product of Toshiba Silicone Corporation) | 2% |
| (10) | Lecithin-treated mica coated titanium**** | 1% |
| (11) | Silicone-treated titanium oxide* | 5% |
| (12) | Silicone-treated, iron oxides (red, yellow, black)* | 3% |
| (13) | 95% ethanol | 15% |

-continued

| | | |
|---|---|---|
| (14) | 1,3-butylene glycol | 2% |
| (15) | Magnesium sulfate | 1% |
| (16) | Water | Balance |
| | | 100% |

*surface-treated to 2% with methylhydrogenpolysiloxane.
**surface-treated to 5% with soybean lecithin.

The components (1) to (7) were heated and mixed at 70° C. Separately, the components (8) to (12) were mixed in a Henschel mixer and then added to the premixed components (1) to (7). The resultant mixture was dispersed and mixed in a mixer. To the resultant mixture, a mixture of the component (13) to (16) which had been to 40° C. was slowly added under stirring over 30 minutes, followed by further stirring for 10 minutes in a homomixer to emulsify same. The thus-formed emulsion was slowly cooled to room temperature under stirring, defoamed and then filled in bottles, so that a liquid foundation was formulated.

EXAMPLE 20

Hand cream

| | | |
|---|---|---|
| (1) | Dimethylpolysiloxane | 10% |
| (2) | Decamethylcyclopentasiloxane | 10% |
| (3) | Dimethylsiloxane-methylstearoxysiloxane copolymer | 3% |
| (4) | Solid paraffin | 1% |
| (5) | Cetanol | 1% |
| (6) | Lanolin | 5% |
| (7) | Poly(N-propionylethyleneimine)-modified silicone (Synthesis Example 9) | 3 |
| (8) | 95% ethanol | 5% |
| (9) | 1,3-butylene glycol | 5% |
| (10) | Sodium hyaluronate | 0.1% |
| (11) | Purified water | balance |
| | | 100% |

The components (1) to (7) were heated to 70° C. and mixed at that temperature. To the resultant mixture, a mixture of the components (8) to (11) was slowly added under stirring over 30 minutes, followed by stirring for 10 minutes in a homomixer to emulsify same. The thus-formed emulsion was defoamed and then filled in polyethylene containers, so that a hand cream was formulated.

EXAMPLE 21

Emulsified, Creamy Cosmetic Preparation

| | | |
|---|---|---|
| (1) | Dimethylpolysiloxane (viscosity 2 cs) | 10% |
| (2) | Decamethylcyclopentasiloxane | 10% |
| (3) | Dimethylsiloxane (viscosity 6 cs) | 5% |
| (4) | Squalane | 5% |
| (5) | Lanolin | 1% |
| (6) | Copolymer (Synthesis Example 10) | 3% |
| (7) | Purified water | Balance |
| (8) | 95% ethanol | 15% |
| (9) | 1,3-butylene glycol | 5% |
| (10) | Sodium hyaluronate | 0.1% |
| | | 100% |

The components (1) to (5) were mixed, to which a mixture of the components (6) to (10) were slowly added under stirring over 30 minutes. The resultant mixture was stirred and emulsified for 10 minutes in a homomixer. The thus-formed emulsion was defoamed and then filled in polyethylene containers, so that an emulsified, creamy cosmetic preparation was formulated.

EXAMPLE 22

Emulsified, Creamy Cosmetic Preparation

An emulsified, creamy cosmetic preparation was formulated in the same manner as in Example 21 except that as the component (6), the copolymer (Synthesis Example 11) was used instead of the copolymer (Synthesis Example 10).

EXAMPLE 23

Emulsified, Creamy Cosmetic Preparation

An emulsified, creamy cosmetic preparation was formulated in the same manner as in Example 21 except that as the component (6), the copolymer (Synthesis Example 12) was used instead of the copolymer (Synthesis Example 10).

EXAMPLE 24

Emulsified, Creamy Cosmetic Preparation

An emulsified, creamy cosmetic preparation was formulated in the same manner as in Example 21 except that as the component (6), the copolymer (Synthesis Example 14) was used instead of the copolymer (Synthesis Example 10).

EXAMPLE 25

Emulsified, Creamy Cosmetic Preparation

An emulsified, creamy cosmetic preparation was formulated in the same manner as in Example 21 except that as the component (6), the copolymer (Synthesis Example 15) was used instead of the copolymer (Synthesis Example 10).

Skin cosmetic preparations, which were composed of the emulsified, water-in-oil compositions of Examples 16 to 25, were excellent in storage stability and as feeling of use, were excellent in refreshed feeling and were stick-free.

What is claimed is:

1. An emulsified, water-in-oil composition comprising the following components (A), (B), (C) and (D):
   (A) an oil phase,
   (B) a high molecular compound having orientation to oil-water interfaces,
   (C) a lower alcohol, and
   (D) water, wherein said component (B) is present in amounts effective for stabilizing said composition in emulsified form.

2. The composition according to claim 1, wherein said component (A) comprises one or more silicone oils.

3. The composition according to claim 1, wherein said component (B) is a solid at room temperature and under normal pressure and forms intra-molecular crosslinks and inter-molecular crosslinks through bonds other than covalent bonds and undergoes neither rupture nor plastic deformation in an elongation range of from 0 to 15% at 20° C. and 65% R.H.

4. The composition according to claim 1, wherein said high molecular compound (B) contains a hydrophilic segment and is soluble or dispersible in water or a lower alcohol.

5. The composition according to claim 1, wherein said high molecular compound (B) is a copolymer containing hydrophilic segments and organosiloxane segments.

6. The composition according to claim 4 or 5, wherein said hydrophilic segment(s) of said high molecular compound (B) has(have) been derived from one or more compounds and/or groups selected from the group consisting of terminal-blocked N-acylalkylene-imines, polyalkylene glycols, polyalkylene glycol monoalkyl ethers, acrylic acid, methacrylic acid, N,N-dimethylacrylamide, dimethylaminoethyl methacrylate, quaternary dimethylaminoethyl methacrylate, methacrylamide, N-t-butylacrylamide, maleic acid, maleic anhydride, half esters of maleic anhydride, chrotonic acid, itaconic acid, acrylamide, acrylate alcohols, hydroxyethyl methacrylate, diallyldimethylammonium chloride, vinylpyrrolidone, vinyl ethers, vinylpyridine, vinylimidazole, styrenesulfonates, allyl alcohol, vinyl alcohol, vinyl caprolactam, N-alkylenecarbobetaines, and saccharide-derived residual groups.

7. The composition according to claim 5, wherein the weight ratio of said hydrophilic segments to said organosiloxane segments in said high molecular compound (B) ranges from 1/50 to 20/1, and the weight average molecular weight of said high molecular compound (B) is from 500 to 500,000.

8. The composition according to claim 1, wherein said high molecular compound (B) contains a hydrophilic segment formed of a poly(N-alkylene-imine) bonded to at least one terminal or side-chain silicon atom of said organopolysiloxane segment via a hetero-atom-containing alkylene group, said poly(N-alkylene-imine) being composed of recurring units represented by the following formula (1):

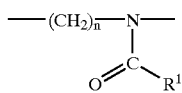

(1)

wherein $R^1$ represents a hydrogen atom, an alkyl group having 1 to 22 carbon atoms, a cycloalkyl group, an aralkyl group or an aryl group, and n stands for a value of 2 or 3.

9. The composition according to claim 1, wherein said high molecular compound (B) is a copolymer formed of an organopolysiloxane segment and poly(N-propylenecarbobetaine) segment bonded to at least one terminal or side-chain silicon atom of said organopolysiloxane segment via a hetero-atom-containing alkylene group, said poly(N-propylenecarbobetaine) segment being composed of recurring units represented by the following formula (2):

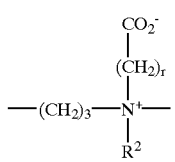

(2)

wherein $R^2$ represents a hydrogen atom, an alkyl group having 1 to 22 carbon atoms, a cycloalkyl group, an aralkyl group, an aryl group or an alkoxycarbonylalkyl group, and r stands for a value of from 1 to 5.

10. The composition according to claim 8 or claim 9, wherein said hetero-atom-containing alkylene group bonded to said at least one terminal or side-chain silicon atom of said organopolysiloxane is selected from the group consisting of groups represented by the following formulas (3):

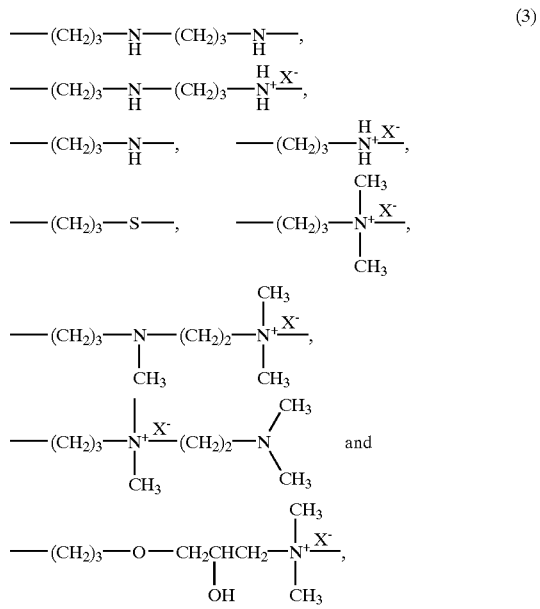

(3)

wherein $X^-$ represents a counter ion to a quaternary ammonium salt.

11. The composition according to claim 1, wherein said high molecular compound (B) is formed of an organopolysiloxane segment and a group bonded to at least one terminal or side-chain silicon atom of said organopolysiloxane segment, said group being represented by the following formula (4):

(4)

wherein m stands for an integer of from 1 to 8.

12. The composition according to claim 11, wherein the number of silicon atoms to which the groups represented by the formula (4) are bonded accounts for 10 to 90% of the total number of silicon atoms in the molecule of said high molecular compound (B), and said high molecular compound (B) has a weight average molecular weight of from 1,000 to 500,000.

13. The composition according to claim 1, wherein said high molecular compound (B) is a copolymer formed of an organopolysiloxane segment and saccharide-derived residual groups which are bonded to at least one terminal or side-chain silicon atoms of said organopolysiloxane segment.

14. The composition according to claim 13, said saccharide-derived residual groups are sugar lactone amidoalkyl groups.

15. The composition according to claim 13, wherein said high molecular compound (B) contains a silicone chain in a proportion of 40–97 wt. % and has a weight average molecular weight of from 1,000 to 500,000.

16. The composition according to claim 15, wherein the weight ratio of said organopolysiloxane segment to said at least one poly(N-propylenecarbobetaine) segment in said high molecular compound (B) ranges from 98/2 to 40/60, and the weight average molecular weight of said high molecular compound (B) is from 1,000 to 500,000.

17. The composition according to claim 1, wherein said component (B) is a copolymer formed of the following segments (i), (ii) and (iii):

| (i) | at least one segment formed of a hydrophobic radical-polymerizable vinyl polymer | 1 to 98 wt. % |
|---|---|---|
| (ii) | at least one segment having hydrophilic polarity | 1.5 to 60 wt. % |
| (iii) | a segment formed of an organopolysiloxane | 0.1 to 90 wt. %. |

18. The composition according to claim 17, wherein said segment (i) has been derived from one or more compounds represented by the following group (5):

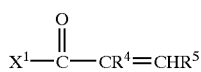  (5)

wherein $X^1$ represents a group selected from the group consisting of —OH, —NH$_2$, —OM (M: a cation), —OR$^3$, —NHR$^3$ and —N(R$^3$)$_2$ (R$^3$: a linear or branched alkyl group having 1 to 8 carbon atoms, N,N-dimethylamino ethyl, 2-hydroxyethyl, 2-methyoxyethyl or 2-ethoxyethyl), and $R^4$ and $R^5$ represent an atom or group selected from the group consisting of a hydrogen atom, a linear or branched alkyl group having 1 to 8 carbon atoms, methoxy, ethoxy, 2-hydroxyethyl, 2-methoxyethyl and ethoxyethyl).

19. The composition according to claim 17, wherein said segment (i) has been derived from one or more compounds selected from the group consisting of the acrylate esters of $C_1$–$C_{18}$ alcohols, the methacrylate esters of $C_1$–$C_{18}$ alkyl, styrene, polystyrene macromers, vinyl acetate, vinyl chloride, vinyl propionate, vinylidene chloride, α-methylstyrene, t-butylstyrene, butadiene, cyclohexadiene, ethylene, propylene and vinyltoluene.

20. The composition according to claim 17, wherein said segment (ii) has been derived from one or more compounds selected from the group consisting of terminal-blocked N-acylalkylene-imines, polyalkylene glycols, polyalkylene glycol monoalkyl ethers, acrylic acid, methacrylic acid, N,N-dimethylacrylamide, dimethylaminoethyl methacrylate, quaternary dimethylaminoethyl methacrylate, methacrylamide, N-t-butylacrylamide, maleic acid, maleic anhydride, half esters of maleic anhydride, chrotonic acid, itaconic acid, acrylamide, acrylate alcohols, hydroxyethyl methacrylate, diallyldimethylammonium chloride, vinylpyrrolidone, vinyl ethers, vinylpyridine, vinylimidazole, styrenesulfonates, allyl alcohol, vinyl alcohol, vinyl caprolactam, N-alkylene-carbobetaines, and saccharide-derived residual groups.

21. The composition according to claim 17, wherein said segment (iii) has been derived from an organopolysiloxane represented by the following formula (6):

  (6)

wherein E represents an oprionally substituted vinyl group copolymerizable with a macromonomer of said segment (i) or (ii), Y represents a divalent connecting group, $R^6$ represents a hydrogen atom, lower alkyl group, aryl group or alkoxy group, $Z^1$ represents a monovalent siloxane polymer moiety having an average molecular weight of at least 500, s stands for 0 or 1, and t stands for an integer of 1 to 3.

22. The composition according to claim 17, wherein said segment (iii) is composed of a silicone-containing macromer which has a weight average molecular weight of from 1,000 to 500,000 and has been formed based on a dimethylpolysiloxane selected from the following formulas:

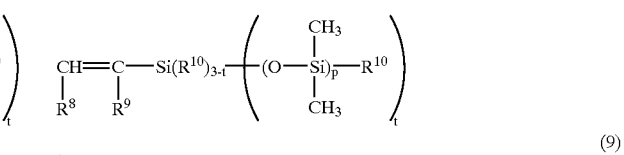

(7)

(8)

(9)

(10)

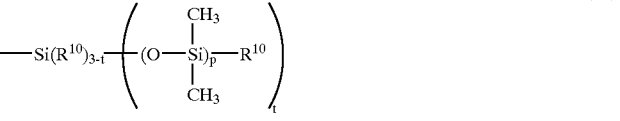

(11)

(12)

wherein $R^7$ represents a hydrogen atom or an alkyl group, $R^8$ represents a hydrogen atom or a carboxyl group, $R^9$ represents a hydrogen atom or a methyl or carboxylmethyl group, $R^{10}$ represents an alkyl, alkoxy, alkylamino, aryl or hydroxyl group, q stands for an integer of from 2 to 6, p stands for an integer of from 5 to 700, s stands for 0 or 1, and t stands for an integer of from 1 to 3.

23. The composition according to claim 1, comprising 10–90 wt. % of said compound (A), 0.05–10 wt. % of said component (B) and 1–40 wt. % of said component (C).

24. A skin cosmetic preparation comprising an emulsified, water-in-oil composition according to claim 1 and at least one additional skin cosmetic additive.

* * * * *